United States Patent
Tam et al.

(10) Patent No.: US 8,340,393 B2
(45) Date of Patent: Dec. 25, 2012

(54) ADVANCED ROUGHNESS METROLOGY

(75) Inventors: Aviram Tam, Nes Ziona (IL); Colin David Chase, Jerusalem (IL)

(73) Assignee: Applied Materials Israel Limited, Rehovot (IL)

( * ) Notice: Subject to any disclaimer, the term of this patent is extended or adjusted under 35 U.S.C. 154(b) by 946 days.

(21) Appl. No.: 10/596,373

(22) PCT Filed: Dec. 10, 2004

(86) PCT No.: PCT/US2004/041884
§ 371 (c)(1),
(2), (4) Date: Dec. 16, 2008

(87) PCT Pub. No.: WO2005/059531
PCT Pub. Date: Jun. 30, 2005

(65) Prior Publication Data
US 2009/0114816 A1    May 7, 2009

Related U.S. Application Data

(60) Provisional application No. 60/528,630, filed on Dec. 10, 2003.

(51) Int. Cl.
*G06K 9/00* (2006.01)
*G01N 23/00* (2006.01)

(52) U.S. Cl. ......... 382/145; 250/311; 382/144; 382/147

(58) Field of Classification Search .................. 348/129, 348/130, 136
See application file for complete search history.

(56) References Cited

U.S. PATENT DOCUMENTS

| 6,480,807 | B1 * | 11/2002 | Miyano | 702/159 |
| 6,839,470 | B2 | 1/2005 | Ikeda | |
| 2003/0021463 | A1 * | 1/2003 | Yamaguchi et al. | 382/145 |
| 2003/0190069 | A1 | 10/2003 | Nikitin et al. | |
| 2003/0194135 | A1 * | 10/2003 | Wenzel | 382/209 |

FOREIGN PATENT DOCUMENTS
EP    1 279 923 A    1/2003
JP    11-257940    9/1999
(Continued)

OTHER PUBLICATIONS

Constantoudis et al., "Quantification of line-edge roughness of photoresists. II. Scaling and fractal analysis and the best roughness descriptors", Apr. 25 2003, Journal of Vacuum Science & Technology B: Microelectronics and Nanometer Structures, vol. 21 Edition3, 1019-1026.*

(Continued)

*Primary Examiner* — Vu Le
*Assistant Examiner* — Kenny Cese
(74) *Attorney, Agent, or Firm* — Tarek N. Fahmi, APC

(57) ABSTRACT

A method for evaluating a feature. The method includes receiving an image of the feature and determining respective coordinates of a plurality of points on an edge of the feature in the image. A figure having a non-circular and non-linear shape is fitted to the plurality of points, and respective distances between the plurality of points and the figure are determined. A roughness parameter for the feature is computed using the respective distances. The method may be applied in the analysis of critical dimensions (CD) of integrated circuits and, particularly, in the measurement of the edge roughness of their features and components as imaged using electron scanning microscopy (SEM).

42 Claims, 5 Drawing Sheets

FOREIGN PATENT DOCUMENTS

| | | |
|---|---|---|
| JP | 11-287630 | 10/1999 |
| JP | 2003-31469 A | 1/2003 |

OTHER PUBLICATIONS

Leunissen et al., "Line edge roughness: experimental results related to a two-parameter model", Mar. 2004, Micro and Nano Engineering, vol. 73-74, pp. 265-270.*

Constantoudis et al., "Quantification of line-edge roughness of photoresists. II. Scaling and fractal analysis and the best roughness descriptors", Apr. 25 2003, Journal of Vacuum Science & Technology B: Microelectronics and Nanometer Structures, vol. 21 Edition 3, pp. 1019-1026.*

Choudhury et al., "Surface roughness prediction in the turning of high-strength steel by factorial design of experiments", May 1997, Journal of Materials Processing Technology, vol. 67, Issues 1-3, pp. 55-61.*

Nelson et al, "Comparison of Metrology Methods for Quantifying the Line Edge Roughness of Patterned Features", Journal of Vacuum Science and Technology B17(6), pp. 2488-2498.

Vandeweyer et al., "The Measurement of Contact Edge Roughness in 193nm Patterning", in Interface 2003, Sep. 2003.

Applied Materials Israel, Ltd, International Search Report and Written Opinion, PCT/US2004/041884, Apr. 27, 2005, pp.

Lee Tae Yong et al.: "Experimental methodology of contact edge roughness on sub-100 nm pattern", Proceedings of SPIE: May 24, 2004, 10 pp.

Bunday Benjamin D et al.: "CD-SEM Measurement of Line Edge Roughness Test Patterns for 193 nm Lithography", Proceedings of SPIE: Jul. 2003, 15 pp.

Applied Materials Israel, Ltd.; JP Application No. 2006-544108; Notice of Reasons for Rejection mailed Mar. 23, 2010, 3pp.

Applied Materials Israel, Ltd.; JP Application No. 2006-544108; Notice of Reasons for Rejection mailed Aug. 17, 2010, 5pp.

Applied Materials Israel, Ltd.; CN Application No. 2004800400189; Notification of the Office Rejection mailed Sep. 4, 2009, 5pp.

Applied Materials Israel, Ltd.; CN Application No. 2004800400189; Notification of the First Office Action mailed Sep. 26, 2008, 11pp.

Applied Materials Israel, Ltd.; CN Application No. 2004800400189; Second Office Action mailed May 8, 2009, 5pp.

Applied Materials Israel, Ltd.; CN Application No. 2004800400189; Third Office Action mailed May 20, 2010, 4pp.

* cited by examiner

ADVANCED ROUGHNESS METROLOGY

CROSS REFERENCES TO RELATED APPLICATIONS

The present patent application is a national phase application of International Application No. PCT/US2004/041884 filed Dec. 10, 2004, which claims priority benefit from U.S. Provisional Application 60/528,630 filed Dec. 10, 2003.

FIELD OF THE INVENTION

The present invention relates generally to measurement of integrated circuits and/or components used in producing the circuits, and specifically to measurement of roughness of features of the integrated circuits and the components.

BACKGROUND OF THE INVENTION

As dimensions of integrated circuit features reduce, the negative effects of roughness of the features, and/or of components such as photo-resist and ancillary structures used to produce the features, become more pronounced since there is no corresponding reduction of roughness with dimension reduction. As a result of the increased problems, metrics that quantify roughness of specific sections of an integrated circuit have been developed; for example, line edge roughness (LER) measures the roughness of a linear edge. One metric for LER that is used in the art is a value of $3\sigma$, where $\sigma$ is the standard deviation of points of the linear edge from a straight line. Other metrics have also been developed.

For example, definitions of edge roughness magnitude and spatial frequency for a linear edge are given by Nelson et al. in an article entitled "Comparison of Metrology Methods for Quantifying the Line Edge Roughness of Patterned Features," in *Journal of Vacuum Science and Technology B*17(6), pages 2488-2498 (1999), which is incorporated herein by reference.

U.S. Patent Application 2003/0190069, to Arkady et al., which is incorporated herein by reference, describes a method for measuring the line edge roughness of an object using a scanning electron microscope. An edge of the object is oriented so that it is non-parallel to a direction of scan and the object is scanned in a line-by-line method. Edge points determined by the scan are fitted to a straight line, and a metric measuring the perpendicular deviation of these points from the line is derived.

U.S. Patent Application 2003/0021463, to Yamaguchi et al., which is incorporated herein by reference, describes a spatial frequency measure for LER. The measure is derived by performing a Fourier transform of points generating a linear edge, and using the Fourier coefficients to generate the frequency measure.

Vandeweyer et al., in an article entitled "The measurement of Contact Edge Roughness in 193 nm patterning," in *Interface* 2003, (September, 2003), which is incorporated herein by reference, describe a process for measuring roughness of contact holes. The process fits edge points of the contacts to a circle, and a metric for the contact edge roughness is defined as the standard variation of the points from the circle.

Notwithstanding the metrics described above, there is a need for a metric that better quantifies roughness of features of an integrated circuit.

SUMMARY OF THE INVENTION

In an embodiment of the present invention, a feature of an object related to production of an integrated circuit is imaged, and coordinates of a set of points of an edge of the feature are determined. The feature may be a contact hole formed in a semiconductor wafer, and the imaging is typically performed using a scanning electron microscope (SEM). A figure having a non-circular and a non-linear shape is fitted to the set of points. The figure may be defined by a function, or may be an arbitrary shape determined from the set of points. Distances, typically perpendicular distances, from the points to the figure are measured, and a processor derives metrics describing the roughness of the feature from the distances. The metrics have been found to give good and internally consistent measures of roughness of the feature.

In one embodiment, a first metric includes a standard deviation of the distances from the points to the figure, taking into account a number of degrees of freedom required to describe the figure. To generate a second metric, the processor determines an auto-correlation function of the distances along the figure, and derives a correlation length between the distances from the function. The correlation length gives a measure of the sharpness of protuberances from the edge of the component part.

For a third metric, the processor performs a Fourier analysis on the distances, and uses the Fourier coefficients to generate an integrated power spectrum of the distances. The Fourier analysis may be performed in the spatial or the frequency domain. A point in the spectrum corresponding to a predetermined percentage of the total power is used as the third metric. Typically, filtering is applied to the coefficients so that not all coefficients are given equal weight in determining the metric. Optionally, the filtering is adjusted according to a manufacturing process that has been used to generate the feature.

In a disclosed embodiment, the figure is assumed to be an ellipse, which has five degrees of freedom.

In an alternative embodiment, two edges of the feature are imaged. The metrics described above are adapted to use distances between the two edges in order to determine corresponding width roughness metrics for the width of the feature.

The present invention will be more fully understood from the following detailed description of the embodiments thereof, taken together with the drawings, a brief description of which follows.

DETAILED DESCRIPTION OF EMBODIMENTS

Figure 1:
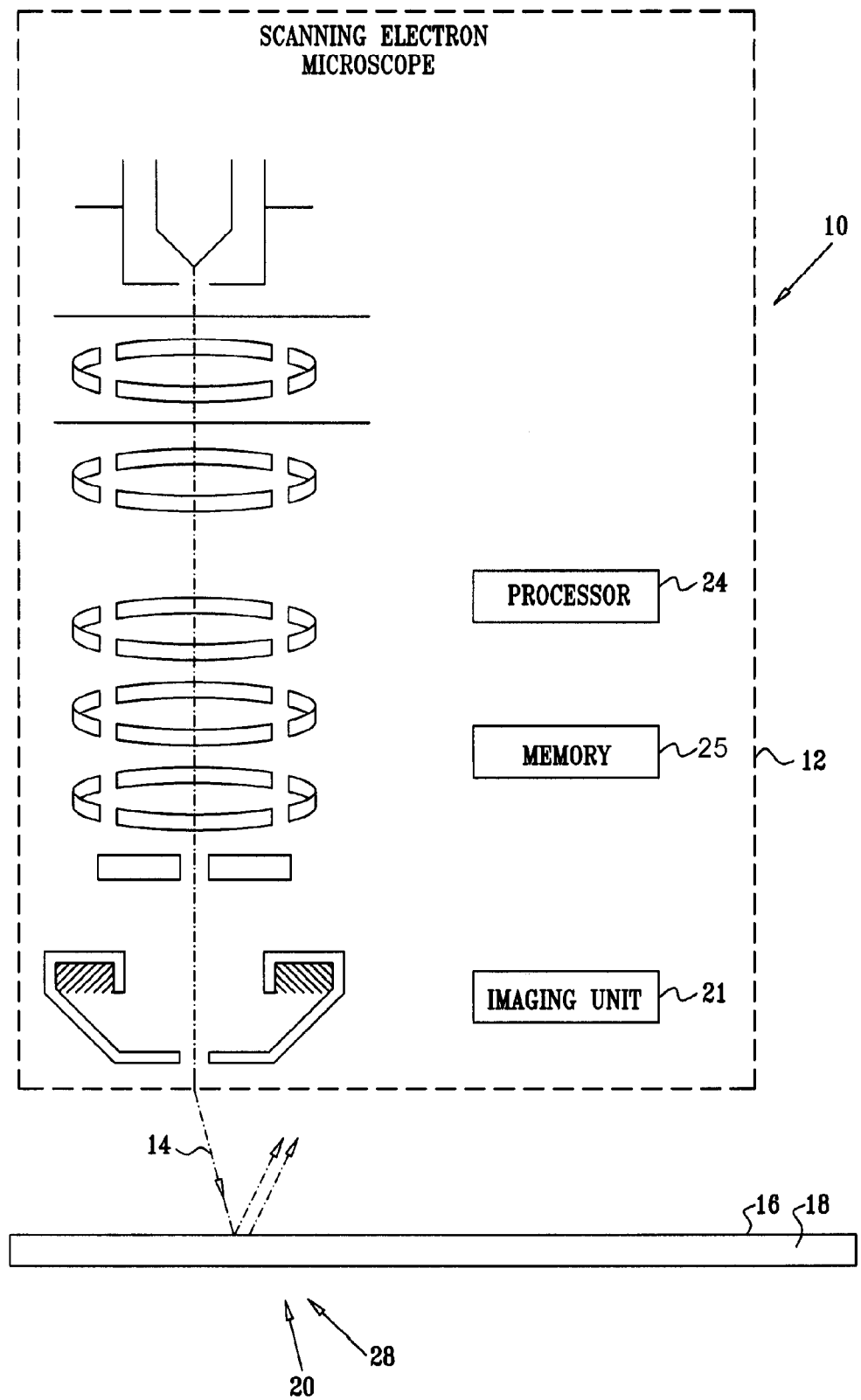
FIG. 1 is a schematic diagram of a semiconductor analysis system, according to an embodiment of the present invention.

Reference is now made to FIG. 1, which is a schematic diagram of a semiconductor analysis system 10, according to an embodiment of the present invention. System 10 includes a scanning electron microscope (SEM) 12, which generates an electron beam 14 that scans a surface 16 of a semiconductor wafer 18. The SEM collects secondary electrons from a feature 20 on the surface, and an imaging unit 21 generates an image of the feature from the secondary electrons. SEM 12 includes a processor 24 and a memory 25 wherein is stored software that enables the processor to operate the SEM, and to perform analyses on the data generated by the SEM. Herein below, unless otherwise stated, feature 20 is assumed to include a contact hole 28, which is illustrated in more detail in FIG. 2. Typically, the image of the contact hole is generated by applying an edge detection algorithm to raw data derived from the secondary electron collection. Methods for generating the raw data and for determining the edge therefrom are well known in the art, and processor 24 applies one or more of these methods to generate the image. Alternatively, the image of feature 20 is generated by another type of microscope known in the art, such as an optical microscope.

While the description herein is generally directed to analysis of a contact hole, it will be understood that the principles of the present invention may be applied to analysis of substantially any microscopic feature having dimensions less than approximately 1 μm. Such features include, but are not limited to, reticles or parts thereof, and "stamps" used as a cast of a structure of a wafer.

Figure 2:
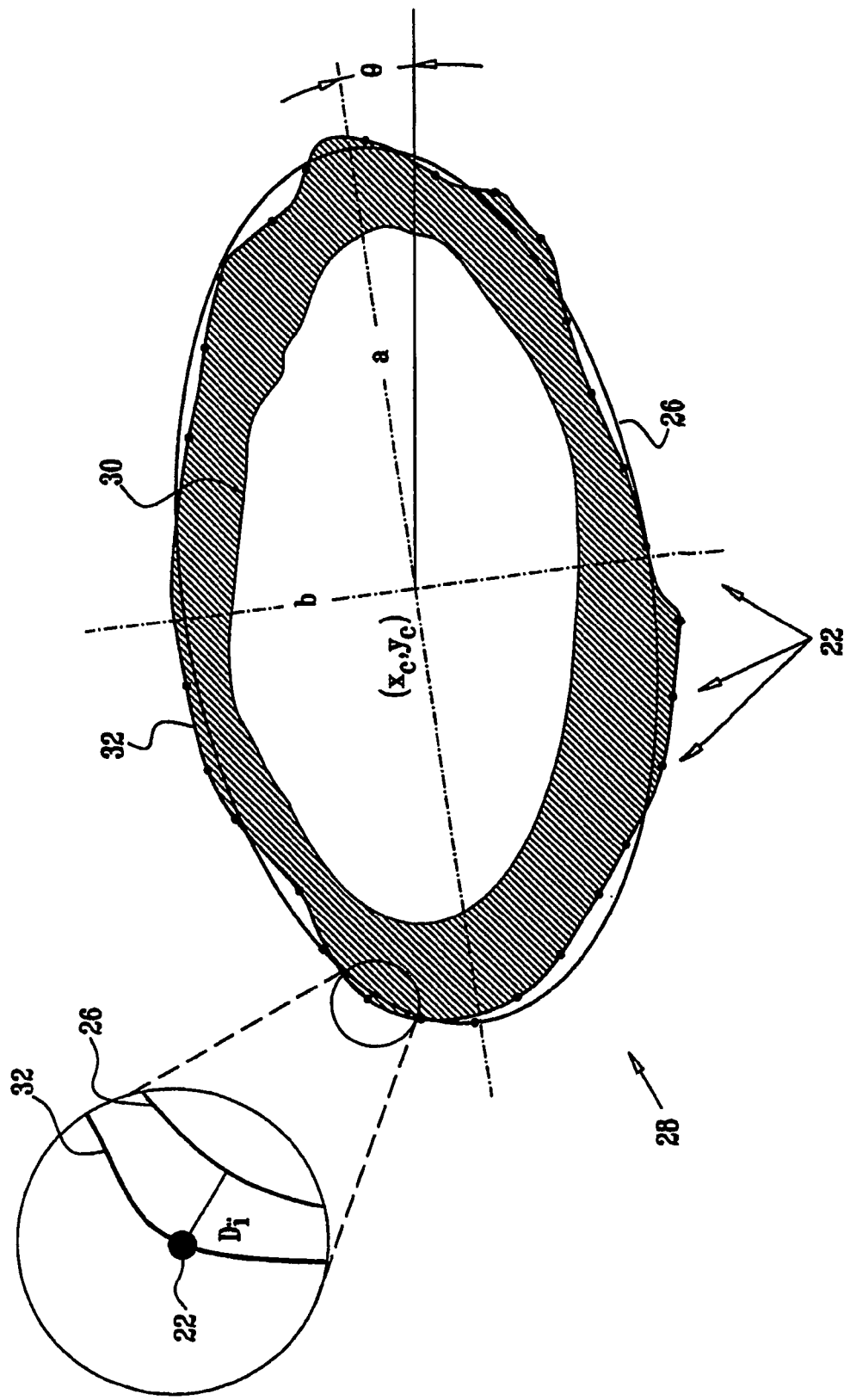
FIG. 2 is a schematic diagram illustrating a contact hole analyzed by the system of FIG. 1, according to an embodiment of the present invention.

FIG. 2 is a schematic diagram illustrating contact hole 28, according to an embodiment of the present invention. Contact hole 28 includes an inner edge 30 and an outer edge 32, and processor 24 is configured to apply the edge detection algorithms to determine an outer set of points 22 on outer edge 32. Points 22 are also referred to herein as points $P_i$, i∈N, where N represents the set of natural numbers. Typically, processor 24 is also configured to determine an inner set of points on inner edge 30. While the analysis described hereinbelow refers only to outer set of points 22 of outer edge 32, it will be appreciated that a substantially similar analysis may be applied to points on the inner edge. For clarity, only points 22 on outer edge 32 are shown in FIG. 2.

Processor 24 is configured to fit the set of points 22 to a closed non-circular FIG. 26, which by way of example is assumed herein to be an ellipse. It will be understood, however, that FIG. 26 may in general be any closed non-circular figure. Typically, an operator of system 10 sets a known shape of the closed non-circular figure to which points 22 are to be fitted. FIG. 26 is in general defined by a number of degrees of freedom. In the case of FIG. 26 being an ellipse, the figure has five degrees of freedom, since the ellipse may be completely defined by two coordinates $(x_c, y_c)$ for the center of the ellipse, the length of the semi-major and semi-minor axes (a, b), where a≠b, and an orientation θ of the ellipse to an arbitrary axis, herein assumed to be a horizontal axis.

After fitting points 22 to FIG. 26, processor 24 calculates values of $D_i$ for each point $P_i$, where $D_i$ is a distance of point $P_i$ to the fitted FIG. 26. In an embodiment of the present invention, $D_i$ is a perpendicular distance to the fitted FIG. 26. In an alternative embodiment, $D_i$ is measured along a line through a center of the fitted figure, and so corresponds to a radial distance. Other methods for determining distances $D_i$ will be apparent to those skilled in the art; all such methods are assumed to be comprised within the scope of the present invention.

Processor 24 derives a first contact edge roughness metric CER for edge 32, using equation (1):

$$CER = 3 \times \sqrt{\frac{\sum_{i=1}^{n} D_i^2}{n - n_{DF}}} \quad (1)$$

where n is the number of points 22, and
$n_{DF}$ is the number of degrees of freedom of the figure fitted to points 22.

For the case of FIG. 26 being an ellipse, equation (1) becomes:

$$CER = 3 \times \sqrt{\frac{\sum_{i=1}^{n} D_i^2}{n - 5}} \quad (2)$$

It will be appreciated that small values of CER correspond to edge 32 fitting closely to FIG. 26, and that a small value of CER typically implies that edge 32 has a low roughness.

Processor 24 is also configured to derive second metrics, herein termed correlation lengths, from the values of $D_i$, as described below.

For each point $P_i$, processor 24 determines a point $P_j$ so that $P_i$, $P_j$ subtend an angle Δθ (0<Δθ<360°) at the center of the ellipse. $P_i$, $P_j$ have corresponding distances $D_i$, $D_j$ to FIG. 26. For each possible value of Δθ, processor 24 calculates a dimensionless auto-correlation function R(Δθ) as follows:

$$R(\Delta\theta) = 1 - \frac{\langle (D_i - D_j)^2 \rangle}{2 \times \frac{\sum_n D_i^2}{n - n_{DF}}} \quad (3)$$

where $\langle x \rangle$ represents the average of all x.

From the values of R(Δθ), a correlation length $CL_{\Delta\theta}$ is determined as the smallest value of Δθ that gives $$R(\Delta\theta) = \frac{1}{e},$$

i.e., as given by equation (4):

$$CL_{\Delta\theta} = \Delta\theta \big|_{R(\Delta\theta) = \frac{1}{e}} \quad (4)$$

Inspection of equations (3) and (4) show that $CL_{\Delta\theta}$ corresponds approximately to an angular periodicity of points $P_i$ relative to FIG. 26. For example, if points $P_i$ are actually generated from an ellipse having 180 evenly distributed "spikes," then $CL_{\Delta\theta}$ is approximately 2°, or the corresponding linear dimension of the ellipse. It will be appreciated that, in general, the smaller the value of $CL_{\Delta\theta}$, the sharper are the protuberances generated by points $P_i$ from FIG. 26, and that as $CL_{\Delta\theta}$ approaches 0, the closer the edge is to being randomly rough. In contrast, as the value of $CL_{\Delta\theta}$ moves from a value of 0, typically the degree of coherence of the roughness increases.

In an alternative embodiment of the present invention, rather than finding points $P_i$ subtending an angle Δθ, processor 24 finds points $P_i$ having an arc length between the points equal to $\Delta L$. The processor then derives an auto-correlation function $R(\Delta L)$, and a correlation length $CL_{\Delta L}$, as given by equations (5) and (6) below. In this case, $CL_{\Delta L}$ is the smallest value of $\Delta L$ that gives $$R(\Delta L) = \frac{1}{e}.$$

$$R(\Delta L) = 1 - \frac{\langle (D_i - D_j)^2 \rangle}{2 \times \frac{\sum_n D_i^2}{n - n_{DF}}} \quad (5)$$

$$CL_{\Delta L} = \Delta L |_{R(\Delta L) = \frac{1}{e}} \quad (6)$$

Hereinbelow, unless otherwise stated, $CL_{\Delta\theta}$ and $CL_{\Delta L}$ are generically termed CL.

To generate a third roughness metric, processor 24 performs a Fourier analysis, typically a Fast Fourier Transform (FFT), on distances $D_i$. The Fourier analysis resolves the distances $D_i$ of points $P_i$ into discrete spectral components, each component having a respective amplitude, according to an equation of the general form of equation (7):

$$D(\theta) = \sum_{m=1}^{\infty} a_m \cos(m\theta) \quad (7)$$

where $D(\theta)$ represents the function of $D_i(\theta)$ vs. $\theta$, and $a_m$ is the amplitude of each component $m\theta$, typically measured in nm.

The coefficients $a_m$ determined by the Fourier analysis are used to generate a power spectrum and an integrated power spectrum for points $P_i$.

Figure 3A:
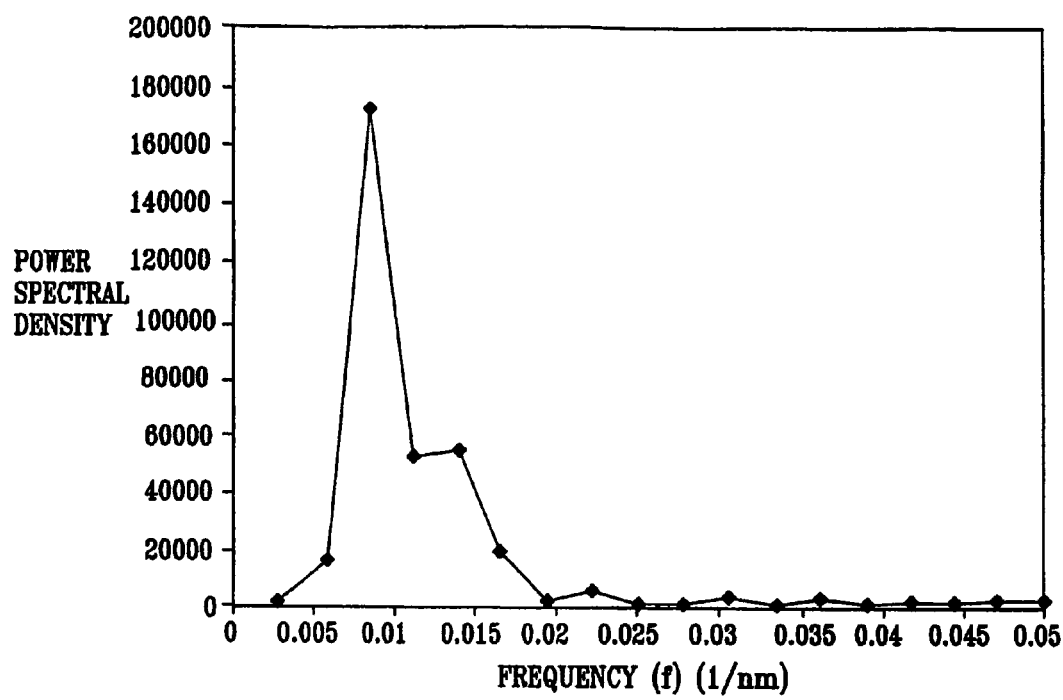
FIGS. 3A and 3B are graphs derived from a Fourier analysis of distances determined in the system of FIG. 1, according to an embodiment of the present invention.
Figure 3B:
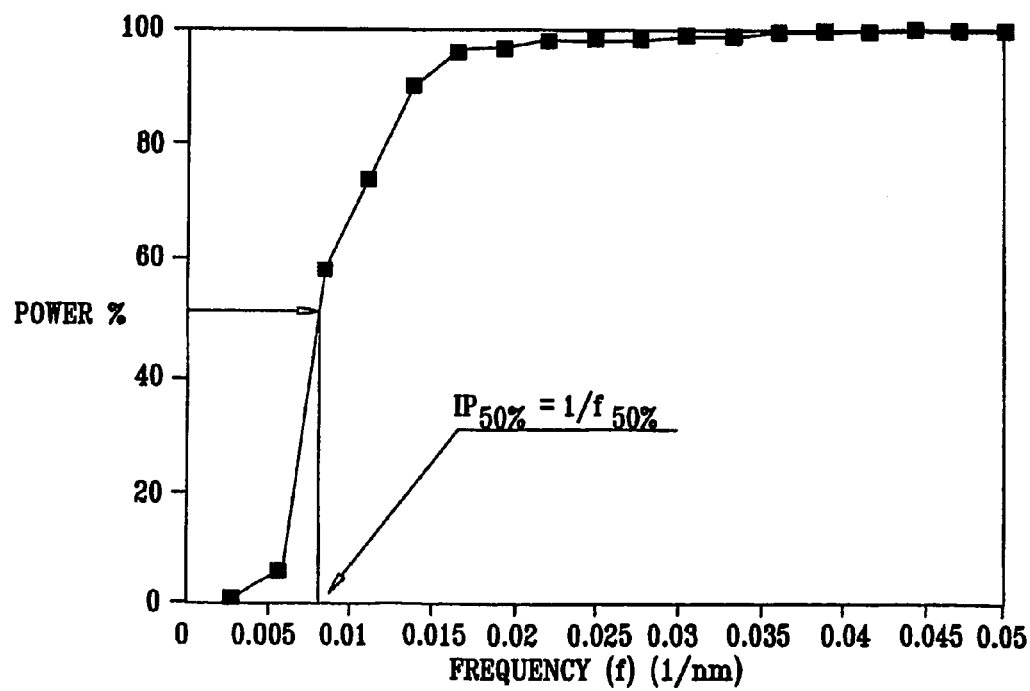

FIGS. 3A and 3B are graphs derived from a Fourier analysis of distances $D_i$, according to an embodiment of the present invention. FIG. 3A illustrates a power spectrum of power spectral density values vs. frequency. FIG. 3B illustrates a corresponding integrated power spectrum of the total percentage power included up to a given frequency vs. frequency. Both graphs are derived by processor 24. From the integrated power spectrum, processor 24 determines an integrated power $IP_p$ for a predetermined value p, where p is a percentage of the power between 0% and 100%, and is typically set to a value between 30% and 70%. In an embodiment illustrated in FIG. 3B, p has a value of 50%, and the value of $Ip_p$ is approximately 0.008 nm$^{-1}$. Processor 24 uses $IP_p$ as a third roughness metric, small values of $IP_p$ corresponding to points $P_i$ having relatively small amplitudes of high frequency protuberances, and large values corresponding to points $P_i$ having relatively large amplitudes of high frequency protuberances.

In an embodiment of the invention, processor 24 filters the values of PS, typically using a band pass, a low pass, or a high pass filter, before determining the value of $IP_p$. The filtration may be applied in either the spatial or the frequency domain, and the filtration, or a process equivalent thereto, may be applied at a stage other than that exemplified here, as will be apparent to those skilled in the art.

The inventors have found that the process used to form contacts, or any other feature on wafer 18, may be a factor in determining values of $a_m$, and the filter may be chosen according to the process used. For example, a mask used to form a photo-resist for the contacts may have its own intrinsic roughness, and this roughness is typically a factor in the roughness of the contacts. Applying a filter determined on the basis of the photo-resist roughness allows the roughness caused by other processes to be measured.

The inventors have also found that the process of filtration may advantageously be applied to isolate and/or eliminate specific shape effects that may obscure a value of $Ip_p$ for substantially any feature on wafer 18. For example, a high pass or a band pass filter may be applied in the frequency domain to reduce or eliminate low frequency values caused by a feature having a shape comprising a relatively low curvature. Other filters that may be used for specific shapes will be apparent to those skilled in the art, and all such filters are assumed to be included in the scope of the present invention.

In experiments performed by the inventors to evaluate the efficacy of using CER and $CL_{\Delta\theta}$ to determine roughness of a contact, two exemplary sets of contacts, each contact being generally similar to contact hole 28, were prepared. A first set of 20 contacts used a first etch recipe, and a second set of 20 contacts used a second etch recipe. Visually, the first set of contacts appeared to be slightly less rough than the second set of contacts. The values of CER and $CL_{\Delta\theta}$ were determined for each contact.

Figure 4:
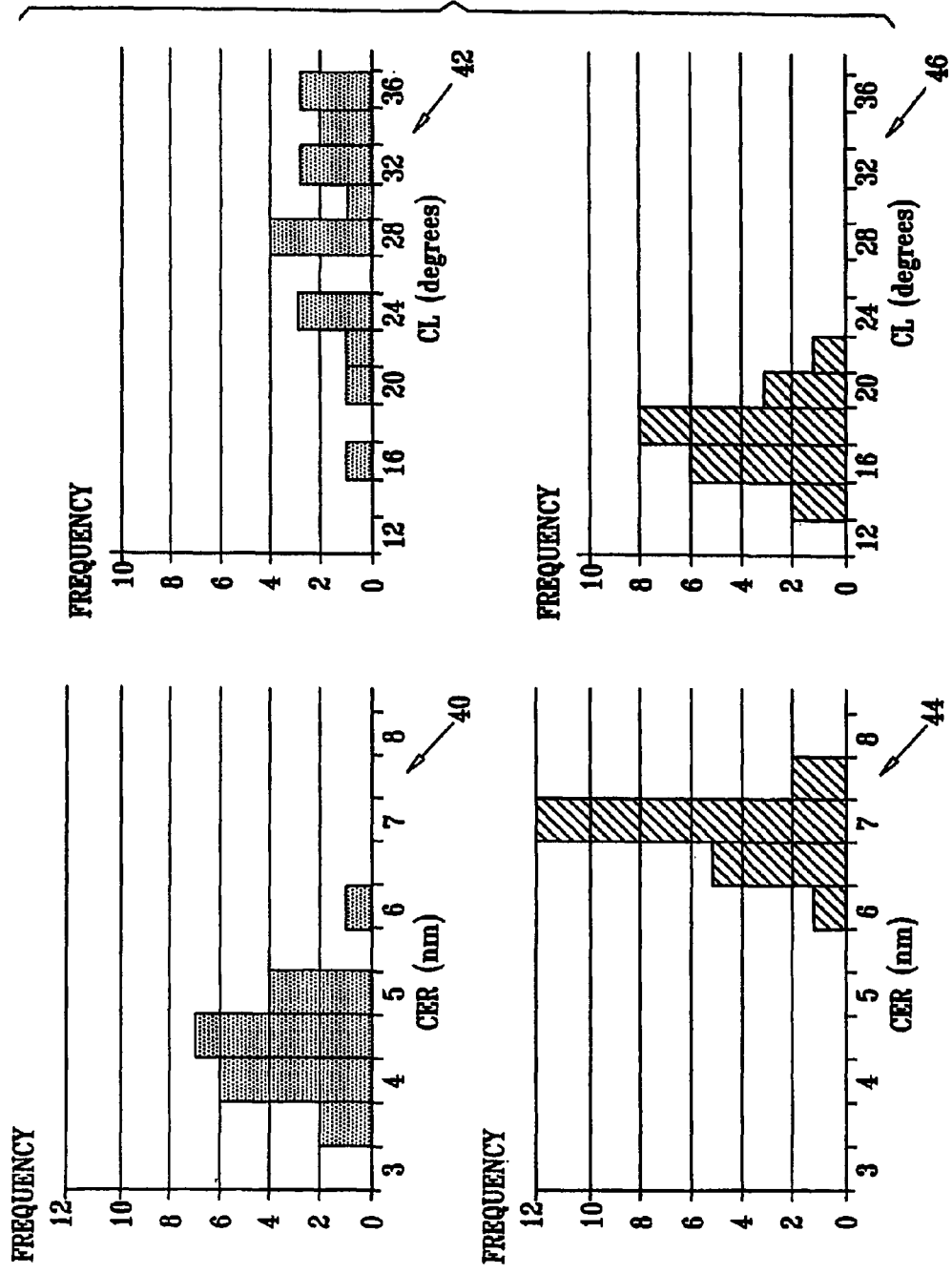
FIG. 4 shows histograms of results of experiments using the system of FIG. 1, according to an embodiment of the present invention.

FIG. 4 shows histograms of the results of the experiments, according to an embodiment of the present invention. Histograms 40 and 42 show frequencies of CER and $CL_{\Delta\theta}$ respectively for the first set of contacts; histograms 44 and 46 show frequencies of CER and $CL_{\Delta\theta}$ respectively for the second set of contacts. The average values for CER and $CL_{\Delta\theta}$ for the two types of contacts are given in Table I below. The values are given with errors assumed to be $3\sigma_{CER}$ or $3\sigma_{CL}$ (where $\sigma_{CER}$ is the standard deviation of CER, and $\sigma_{CL}$ is the standard deviation of $CL_{\Delta\theta}$).

TABLE I

|  | CER ± $3\sigma_{CER}$ | $CL_{\Delta\theta}$ ± $3\sigma_{CL}$ |
| --- | --- | --- |
| First Set | 4.13 ± 0.23 | 28.41 ± 1.34 |
| Second Set | 6.60 ± 0.32 | 16.51 ± 0.45 |

Inspection of FIG. 4 and of Table I shows that for both metrics the two sets of results are well separated. Thus, CER acts as good first metric of roughness, smaller values of CER corresponding to less rough contacts. Also, CL acts as good second metric of roughness, larger values of CL corresponding to less rough contacts.

It will be understood that while the descriptions above relates generally to fitting an edge to a closed figure in the shape of an ellipse, the closed figure may have substantially any predetermined noncircular shape. For example, the shape of the closed figure may be represented by an equation of the form:

$$\left(\frac{x}{a}\right)^n + \left(\frac{y}{b}\right)^n = 1 \quad (8)$$

where n>2. In this case, "a" may or may not be equal to "b".

Those skilled in the art will be able to adapt the derivations of the metrics described herein, mutatis mutandis, to accommodate alterations such as differing numbers of degrees of freedom of the predetermined non-circular shape.

The inventors have found that the correlation coefficients CL described above give good metrics of roughness for edges of features having substantially any shape. Consequently, in an alternative embodiment of the present invention, the figure fitted to the edge includes substantially any closed or open figure. In this case, metrics used to determine the roughness of the edge are substantially those given by equations (4) and (6) above, mutatis mutandis.

In a further alternative embodiment of the present invention, rather than fitting the experimentally determined points to a specific figure, processor 24 uses the points to fit a nominal shape, or "figure backbone," to the points. The nominal shape derived depends on the experimentally determined points, and may be substantially any non-linear shape. The nominal shape is typically generated by averaging positions of sub-sets of the points, by methods which are well known in the art. Once the averaged positions of the nominal shape have been determined, processor 24 determines distances of the points to the nominal shape, and uses these distances to calculate values of CER, CL, and/or $Ip_p$, substantially as described above with respect to equations (1), (3)-(7), and FIGS. 3A and 3B. The distances are typically measured at substantially equal intervals along the nominal shape; alternatively, the distances may be measured at unequal intervals along the shape. It will be appreciated that the number of degrees of freedom $n_{DF}$ used in equations (1), (3) and (5) is dependent on the method used to generate the nominal shape.

It will be understood that the metrics described above may be used, mutatis mutandis, to generate metrics which may be applied to measure a width roughness of a feature having two edges. For example, equation (1) may be adapted to give an expression for a contact width roughness (CWR):

$$CWR = 3 \times \sqrt{\frac{\sum_{i=1}^{n} \Delta D_i^2}{n}} \quad (9)$$

where $\Delta D_i$ is a distance between corresponding points $P_i$ on the two edges.

Adaptations to equations (3)-(7) using $\Delta D_i$, and corresponding alterations to the process described with respect to FIGS. 3A and 3B, in order to generate width metrics corresponding to the edge metrics described above, will be apparent to those skilled in the art. All such adaptations and alterations are assumed to be comprised within the scope of the present invention.

Figure 5:
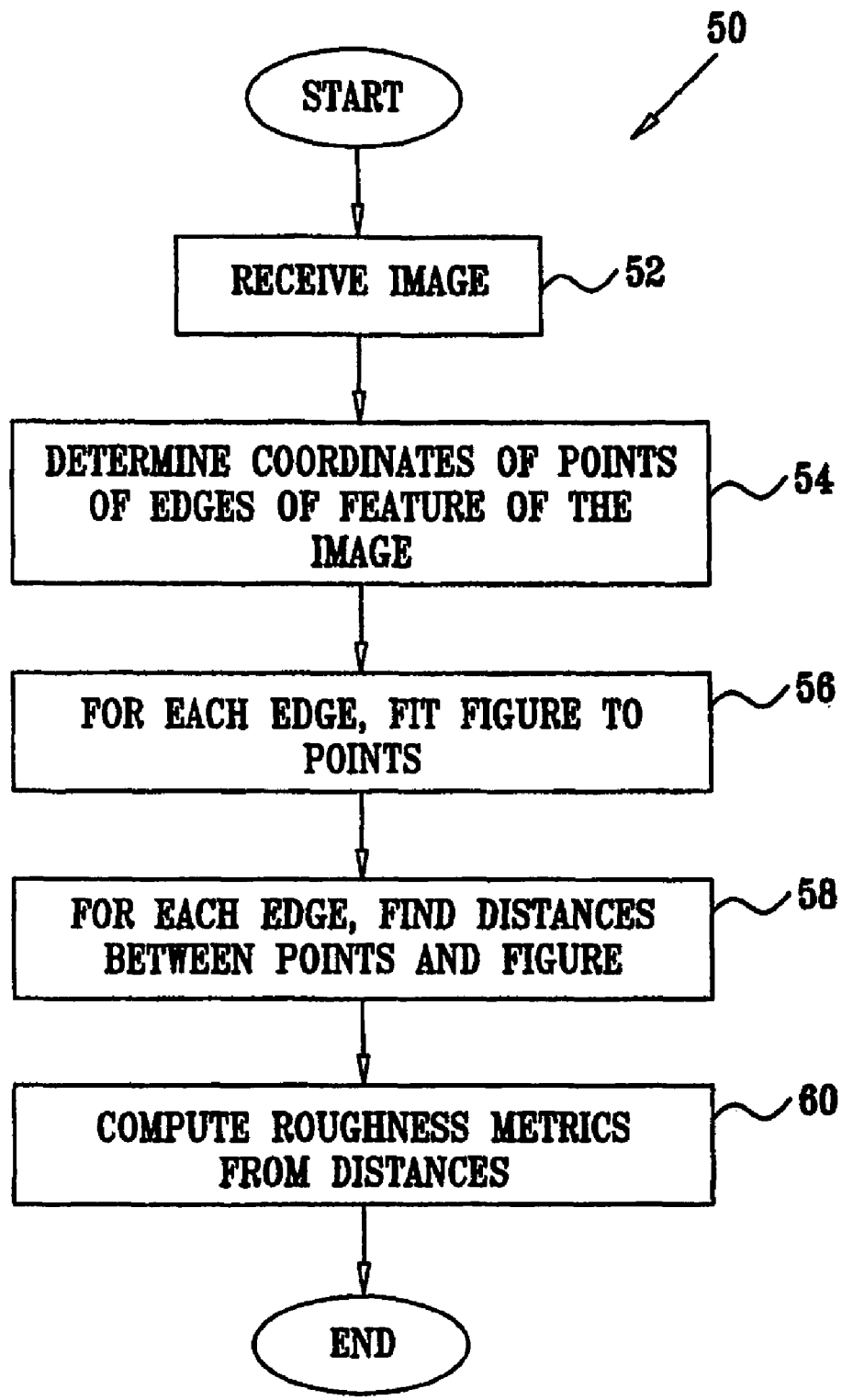
FIG. 5 is a flowchart showing steps used to derive roughness metrics, according to an embodiment of the present invention.

FIG. 5 is a flowchart 50 showing steps used to derive roughness metrics, according to an embodiment of the present invention. By way of example, it is assumed that two edges of a feature are imaged, and the roughness metrics are computed using both sets of edges. In a first step 52, an image of the feature to be measured is generated, substantially as described above with reference to FIG. 1. In a second step 54, coordinates of points for each of the edges of the feature are determined. In a fitting step 56, for each edge the points determined in step 54 are fitted to a figure, generally as described above with reference to FIG. 2. Alternatively, a nominal shape for each of the edges is generated from the coordinates of the points of the respective edge, as described above. In a distance-measuring step 58, distances between the figure or the nominal shape and the points are calculated. In a final step 60, the values of the distances are used to calculate the roughness metrics, substantially as described above with reference to equations (1), (3)-(7), (9), and/or FIGS. 3A and 3B.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for evaluating a feature, comprising:
   receiving an image of the feature;
   determining respective coordinates of a plurality of points on an edge of the feature in the image;
   fitting a figure having a non-circular and non-linear shape to the plurality of points;
   thereafter determining respective distances between the plurality of points and the figure having the non-circular and non-linear shape; and
   computing at least one roughness parameter for the feature using the respective distances, wherein computing the at least one roughness parameter further comprises computing a correlation length (CL) based on a sum of squares of the respective distances, a number of degrees of freedom of the figure, and an average of squares of differences of the respective distances.

2. The method according to claim 1, wherein computing the at least one roughness parameter further comprises performing a Fourier analysis of the respective distances, and generating a power spectrum based on the Fourier analysis.

3. The method according to claim 2, wherein generating the power spectrum comprises filtering results of the Fourier analysis.

4. The method according to claim 3, wherein filtering the results comprises selecting a filter based on a process used to form the feature.

5. The method according to claim 1, wherein the feature is formed on a substrate, and wherein the feature and the substrate are part of a semiconductor wafer.

6. The method according to claim 5, wherein the feature comprises a contact hole.

7. The method according to claim 1, wherein receiving the image comprises generating the image with a scanning electron microscope.

8. The method according to claim 1, wherein the figure comprises an ellipse.

9. The method according to claim 1, wherein the figure has a known shape.

10. The method according to claim 1, wherein fitting the figure comprises determining a nominal shape of the figure by averaging at least some of the plurality of points.

11. The method according to claim 1, wherein the figure is a closed figure.

12. The method according to claim 1, wherein the distance is a perpendicular distance to the figure or a radial distance.

13. The method according to claim 1, wherein the feature is a reticle, a part of the reticle, or a cast of a structure.

14. A method for evaluating a feature, comprising:
   receiving an image of the feature;
   determining respective coordinates of a first plurality of points on a first edge of the feature in the image;
   fitting a first figure having a first non-circular and non-linear shape to the first plurality of points;
   determining respective coordinates of a second plurality of points on a second edge of the feature in the image;
   fitting a second figure having a second non-circular and non-linear shape to the second plurality of points;

thereafter determining respective distances between the first plurality of points and the first figure having the first non-circular and non-linear shape and respective distances between the second plurality of points and the second figure having the second non-circular and non-linear shape; and computing a roughness parameter for the feature in response to the respective distances.

15. The method according to claim 14, wherein computing the at least one roughness parameter further comprises performing a Fourier analysis of the respective distances, and generating a power spectrum based on the Fourier analysis.

16. The method according to claim 15, wherein generating the power spectrum comprises filtering results of the Fourier analysis.

17. The method according to claim 16, wherein filtering the results comprises selecting a filter based on a process used to form the feature.

18. The method according to claim 14, wherein the feature is formed on a substrate, and wherein the feature and the substrate are part of a semiconductor wafer.

19. The method according to claim 18, wherein the feature comprises a contact hole.

20. The method according to claim 14, wherein receiving the image comprises generating the image with a scanning electron microscope.

21. The method according to claim 14, wherein the figure comprises an ellipse.

22. The method according to claim 14, wherein the figure has a known shape.

23. The method according to claim 14, wherein fitting the figure comprises determining a nominal shape of the figure by averaging at least some of the plurality of points.

24. The method according to claim 14, wherein the figure is a closed figure.

25. The method according to claim 14, wherein the distance is a perpendicular distance to the figure or a radial distance.

26. The method according to claim 14, wherein the feature is a reticle, a part of the reticle, or a cast of a structure.

27. Apparatus for evaluating a feature, comprising:
an imaging unit adapted to generate an image including the feature; and
a processor adapted to:
determine respective coordinates of a plurality of points on an edge of the feature in the image,
fit a figure having a non-circular and non-linear shape to the plurality of points,
thereafter determine respective distances between the plurality of points and the figure having the non-circular and non-linear shape, and
compute at least one roughness parameter for the feature in response to the respective distances, wherein the at least one roughness parameter comprises a correlation length (CL), and the CL is computed based on a sum of squares of the respective distances, a number of degrees of freedom of the figure, and an average of squares of differences of the respective distances.

28. The apparatus according to claim 27, wherein computing the at least one roughness parameter comprises performing a Fourier analysis of the respective distances, and wherein the processor is further adapted to generate a power spectrum based on the Fourier analysis.

29. The apparatus according to claim 28, wherein generating the power spectrum comprises filtering results of the Fourier analysis.

30. The apparatus according to claim 29, wherein the filtering comprises selecting a filter based on a process used to form the feature.

31. The apparatus according to claim 27, wherein the feature is formed on a substrate, and wherein the substrate and the feature are part of a semiconductor wafer.

32. The apparatus according to claim 31, wherein the feature comprises a contact hole.

33. The apparatus according to claim 27, wherein the imaging unit and the processor are part of a scanning electron microscope.

34. The apparatus according to claim 27, wherein the figure comprises an ellipse.

35. The apparatus according to claim 27, wherein the figure has a known shape.

36. The apparatus according to claim 27, wherein the processor is further adapted to determine a nominal shape of the figure by averaging at least some of the plurality of points.

37. The apparatus according to claim 27, wherein the figure is a closed figure.

38. The apparatus according to claim 27, wherein the distance is a perpendicular distance to the figure or a radial distance.

39. The apparatus according to claim 27, wherein the feature is a reticle, a part of the reticle, or a cast of a structure.

40. Apparatus for evaluating a feature, comprising:
an imaging unit adapted to generate an image including the feature; and
a processor adapted to:
determine respective coordinates of a first plurality of points on a first edge of the feature in the image,
fit a first figure having a first non-circular and non-linear shape to the first plurality of points,
determine respective coordinates of a second plurality of points on a second edge of the feature in the image,
fit a second figure having a second non-circular and non-linear shape to the second plurality of points,
thereafter determine respective distances between the first plurality of points and the first figure having the first non-circular and non-linear shape and respective distances between the second plurality of points and the second figure having the second non-circular and non-linear shape, and
compute a roughness parameter for the feature in response to the respective distances.

41. A method for evaluating a feature, comprising:
receiving an image of the feature;
determining respective coordinates of a plurality of points on an edge of the feature in the image;
fitting a figure having a non-circular and non-linear shape to the plurality of points;
thereafter determining respective distances between the plurality of points and the figure having the non-circular and non-linear shape; and
computing a correlation length based on a sum of squares of the respective distances, a number of degrees of freedom of the figure, and an average of squares of differences of the respective distances.

42. Apparatus for evaluating a feature, comprising:
an imaging unit adapted to generate an image including the feature; and
a processor adapted to:
determine respective coordinates of a plurality of points on an edge of the feature in the image,
fit a figure having a non-circular and non-linear shape to the plurality of points, thereafter determine respective distances between the plurality of points and the figure having the non-circular and non-linear shape, and
compute a correlation length based on a sum of squares of the respective distances, a number of degrees of freedom of the figure, and an average of squares of differences of the respective distances.

* * * * *